US012768834B2

(12) United States Patent
Stevens Bastos et al.

(10) Patent No.: US 12,768,834 B2
(45) Date of Patent: Oct. 20, 2026

(54) ABSORBENT BIOGENIC LITTER MIXTURE COMPOSITION

(71) Applicant: Petfive Brands Holding LLC, Fort Lauderdale, FL (US)

(72) Inventors: Pedro Eduardo Stevens Bastos, Sao Paulo (BR); Gustavo Tallia Loducca, Sao Paulo (BR); Isadora Duarte Sabater, Sao Paulo (BR)

(73) Assignee: Petfive Brands Holding LLC, Fort Lauderdale, FL (US)

( * ) Notice: Subject to any disclaimer, the term of this patent is extended or adjusted under 35 U.S.C. 154(b) by 0 days.

(21) Appl. No.: 19/294,892

(22) Filed: Aug. 8, 2025

(65) Prior Publication Data

US 2026/0043794 A1 Feb. 12, 2026

Related U.S. Application Data

(60) Provisional application No. 63/681,512, filed on Aug. 9, 2024.

(51) Int. Cl.
*G01N 33/52* (2006.01)
*A01K 1/01* (2006.01)
*A01K 1/015* (2006.01)

(52) U.S. Cl.
CPC ......... *G01N 33/528* (2013.01); *A01K 1/0155* (2013.01); *G01N 2800/34* (2013.01)

(58) Field of Classification Search
CPC . A01K 1/0155; G01N 33/528; G01N 2800/34
USPC .......................................................... 436/163
See application file for complete search history.

(56) References Cited

U.S. PATENT DOCUMENTS

| | | | | |
|---|---|---|---|---|
| 4,727,824 A * | 3/1988 | Ducharme | A01K 1/0155 | 119/171 |
| 5,060,598 A * | 10/1991 | Richards | A01K 1/0155 | 119/171 |
| 5,152,250 A * | 10/1992 | Loeb | A01K 1/0155 | 119/171 |
| 5,176,107 A * | 1/1993 | Buschur | A01K 1/0154 | 119/172 |
| 5,468,450 A | 11/1995 | Michael | | |
| 6,019,062 A * | 2/2000 | Lombard | A01K 1/0152 | 119/172 |
| 6,162,646 A | 12/2000 | Webster et al. | | |
| 6,376,252 B1 | 4/2002 | Van Lente et al. | | |
| 6,444,169 B1 | 9/2002 | Evtodienko et al. | | |
| 6,568,349 B1 * | 5/2003 | Hughes | A01K 1/0155 | 119/171 |

(Continued)

FOREIGN PATENT DOCUMENTS

| | | |
|---|---|---|
| CA | 2582967 A1 | 10/2007 |
| CA | 2623328 A1 | 8/2009 |

(Continued)

OTHER PUBLICATIONS

Vaughn, S. F. et al, Industrial Crops and Products 2013, 43, 798-801. (Year: 2013).*

(Continued)

*Primary Examiner* — Arlen Soderquist
(74) *Attorney, Agent, or Firm* — Fish & Richardson P.C.

(57) ABSTRACT

An absorbent biogenic composition includes a mixture of a base material, a plant-based oil, and a plant-based pH indicator.

30 Claims, 3 Drawing Sheets

(56) References Cited

U.S. PATENT DOCUMENTS

| | | | | |
|---|---|---|---|---|
| 6,682,937 | B2 | 1/2004 | Evtodienko et al. | |
| 7,033,990 | B2 | 4/2006 | Dundale et al. | |
| 7,426,902 | B1 * | 9/2008 | Doering | A01K 1/0155 119/171 |
| 7,533,630 | B2 | 5/2009 | Steekel et al. | |
| 8,540,945 | B2 | 9/2013 | Ito et al. | |
| 8,733,288 | B2 | 5/2014 | Winkleman et al. | |
| 9,883,653 | B2 * | 2/2018 | Provenzano | A01K 1/0155 |
| 10,583,420 | B2 | 3/2020 | Jollez et al. | |
| 10,660,301 | B1 | 5/2020 | Rotman | |
| 10,908,150 | B2 | 2/2021 | Jollez | |
| 11,013,823 | B2 | 5/2021 | Jollez et al. | |
| 11,806,691 | B2 | 11/2023 | Vanghn et al. | |
| 2001/0012636 | A1 * | 8/2001 | Azar | G01N 33/84 426/106 |
| 2001/0047769 | A1 * | 12/2001 | McPherson | A01K 1/0155 119/171 |
| 2003/0170905 | A1 | 9/2003 | Kamyshny et al. | |
| 2003/0205204 | A1 * | 11/2003 | Wang | A01K 1/0155 119/171 |
| 2007/0277739 | A1 * | 12/2007 | Wang | A01K 1/0155 119/161 |
| 2009/0084322 | A1 * | 4/2009 | Axelrod | A01K 1/0152 119/171 |
| 2009/0255478 | A1 * | 10/2009 | Wadams | A01K 1/0155 119/173 |
| 2010/0116215 | A1 * | 5/2010 | Hughes | A01K 1/0155 119/171 |
| 2011/0084027 | A1 * | 4/2011 | Hughes | A01K 1/0155 210/660 |
| 2012/0202236 | A1 * | 8/2012 | Jollez | A01K 1/0155 435/28 |
| 2012/0230884 | A1 * | 9/2012 | Ito | B01J 20/3293 427/212 |
| 2012/0288468 | A1 * | 11/2012 | Wang | A01K 1/0155 424/76.6 |
| 2012/0288955 | A1 * | 11/2012 | Ito | A61L 15/60 436/163 |
| 2013/0213309 | A1 * | 8/2013 | Wang | A01K 1/0155 119/165 |
| 2013/0213312 | A1 * | 8/2013 | Wang | A01K 1/011 119/171 |
| 2013/0213313 | A1 * | 8/2013 | Wang | B01J 20/24 264/109 |
| 2013/0213314 | A1 * | 8/2013 | Wang | B29C 44/54 264/41 |
| 2014/0000525 | A1 * | 1/2014 | Schumski | A01K 1/0154 106/501.1 |
| 2014/0000526 | A1 * | 1/2014 | Kuras | A01K 1/0107 119/173 |
| 2014/0165921 | A1 * | 6/2014 | Raymond | A01K 1/0155 427/180 |
| 2015/0128869 | A1 * | 5/2015 | Raymond | A01K 1/0154 119/172 |
| 2017/0000079 | A1 * | 1/2017 | Lau | A01K 1/0155 |
| 2017/0127644 | A1 * | 5/2017 | Provenzano | A01K 1/0152 |
| 2017/0332654 | A1 * | 11/2017 | Everard | C11B 5/0092 |
| 2018/0111884 | A1 * | 4/2018 | Hoff | C05F 11/02 |
| 2018/0229218 | A1 * | 8/2018 | Jollez | B01J 20/262 |
| 2019/0000033 | A1 * | 1/2019 | Wang | A01K 1/0154 |
| 2019/0117823 | A1 * | 4/2019 | Jollez | B01J 20/3293 |
| 2019/0274274 | A1 * | 9/2019 | Huck | A01K 1/0155 |
| 2022/0097021 | A1 * | 3/2022 | Vaughn | B01J 20/3042 |
| 2024/0009650 | A1 | 1/2024 | Murphy | |
| 2024/0099261 | A1 * | 3/2024 | Lipscomb | B01J 20/3295 |
| 2024/0107975 | A1 * | 4/2024 | Gandikota | A01K 1/0155 |
| 2025/0000050 | A1 * | 1/2025 | Drief | A01K 1/0155 |
| 2026/0043794 | A1 * | 2/2026 | Stevens Bastos | A01K 1/0152 |

FOREIGN PATENT DOCUMENTS

| | | | | |
|---|---|---|---|---|
| CN | 101672799 A | | 3/2010 | |
| CN | 105445212 A | | 6/2016 | |
| CN | 109497425 A | * | 3/2019 | A23B 2/788 |
| CN | 109596455 A | | 4/2019 | |
| CN | 110583496 A | | 12/2019 | |
| CN | 111024691 A | | 4/2020 | |
| CN | 111587797 A | * | 8/2020 | A01K 1/0155 |
| CN | 111781200 A | | 10/2020 | |
| CN | 111973635 A | | 11/2020 | |
| CN | 112352685 A | | 2/2021 | |
| CN | 112673969 A | | 4/2021 | |
| CN | 112715385 A | | 4/2021 | |
| CN | 112715387 A | | 4/2021 | |
| CN | 113439669 A | | 9/2021 | |
| CN | 114609129 A | | 6/2022 | |
| CN | 114617069 A | | 6/2022 | |
| CN | 115825394 A | | 3/2023 | |
| CN | 116026823 A | | 4/2023 | |
| CN | 116158356 A | | 5/2023 | |
| CN | 116210395 A | | 6/2023 | |
| CN | 116794022 A | | 9/2023 | |
| CN | 116814539 A | | 9/2023 | |
| CN | 116849097 A | | 10/2023 | |
| CN | 116930163 A | | 10/2023 | |
| CN | 116953243 A | | 10/2023 | |
| CN | 117296722 A | | 12/2023 | |
| CN | 117502253 A | | 2/2024 | |
| CN | 118140822 A | * | 6/2024 | A01K 1/0155 |
| DE | 102004046102 A1 | | 4/2006 | |
| EP | 2433127 B1 | | 4/2014 | |
| ES | 2259514 A1 | | 10/2006 | |
| JP | 1995264948 A | | 10/1995 | |
| JP | 1996510321 A | | 10/1996 | |
| JP | 2006234475 A | | 9/2006 | |
| JP | 2009261318 A | | 11/2009 | |
| WO | WO 199628538 A1 | | 9/1996 | |
| WO | WO-0150843 A2 | * | 7/2001 | A01K 1/0152 |
| WO | WO 2009075601 A1 | | 6/2009 | |
| WO | WO 2017/165953 A1 | | 10/2017 | |
| WO | WO 2019109184 A1 | | 6/2019 | |
| WO | WO 2023/283674 A1 | | 1/2023 | |
| WO | WO 2023172715 A1 | | 9/2023 | |

OTHER PUBLICATIONS

Ezati, P. et al, International Journal of Biological Macromolecules 2019, 132, 157-165. (Year: 2019).*

Saikeaw, N. et al, E3S Web of Conferences 2021, 302, Article 02017, 8 pages. (Year: 2021).*

De Nisi, P. et al, ACS Sustainable Chemistry & Engineering Sep. 2021, 3781-3791 with 5 pages of supporting information. (Year: 2021).*

International Search Report and Written Opinion in International Appln. No. PCT/US2025/041351, mailed on Dec. 23, 2025, 18 pages.

Petfive Brands, "Sustainably Yours" Cat Litter. Screenshots from www.sylitter.com from Mar. 12, 2019, available on Wayback Machine (http://search.archive.org) downloaded Apr. 17, 2026; 2 pages.

* cited by examiner

ABSORBENT BIOGENIC LITTER MIXTURE COMPOSITION

CROSS-REFERENCE TO RELATED APPLICATION

This application claims the benefit of U.S. patent application Ser. No. 63/681,512, filed on Aug. 9, 2024, entitled “Absorbent Biogenic Composition,” which is incorporated by reference herein in its entirety.

TECHNICAL FIELD

This invention relates to an absorbent biogenic composition and a method of making same.

BACKGROUND

Urine is a body fluid resulting from biological processes and physiological systems, typically involving the kidneys which filter waste products from the bloodstream. Factors such as diet, hydration habits, and physical, mental, and behavioral health affect the composition, concentration, quantity, and pH of urine. The properties of an animal's urine can serve as an indicator of health conditions such as, but not limited to, proper or improper bladder or kidney function. Indoor animals typically use a litter box for urination, and various types of animal litter are available to manage this waste.

SUMMARY

This disclosure describes an absorbent biogenic composition with a plant-based pH indicator, as well as methods of making the absorbent biogenic composition.

In a first general aspect, an absorbent biogenic composition includes a mixture of a base material, a plant-based oil, and a plant-based pH indicator.

Implementations of the first general aspect may include one or more of the following features.

The absorbent biogenic composition is a clumping litter (e.g., a clumping animal litter). The absorbent biogenic composition may include at least about 98 wt % of the base material. The base material may include a starch, a flour, gum, fiber, polysaccharide, protein, cellulose, lignin, or any combination thereof. The starch may include corn starch, potato starch, rice starch, pea starch, soybean starch, or cassava starch. The flour may include corn flour, cassava flour, or soybean flour.

The absorbent biogenic composition may include about 0.1 wt % to about 1.0 wt % of the plant-based oil. The plant-based oil may include sunflower oil, corn oil, canola oil, cottonseed oil, soybean oil, or any combination thereof.

The absorbent biogenic composition may include about 0.001 wt % to about 1.0 wt % of the plant-based pH indicator. The plant-based pH indicator is an extract, a pigment, or any combination thereof. The plant-based pH indicator may include one or more flavonoids. The one or more flavonoids may include flavones, isoflavonoids, neoflavonoids, anthocyanins, or a combination thereof. Red, brown, orange, yellow, blue, purple, and black fruits and vegetables include, but are not limited to, black carrots, purple carrots, cabbage, red cabbage, berries, red onions, kidney beans, pomegranates, grapes, tomatoes, acai, or any combination thereof. The berries may include, but are not limited to, blackcurrants, blackberries, blueberries, cranberries, raspberries, strawberries, or any combination thereof.

The one or more flavonoids are derived from red, brown, orange, yellow, blue, purple, and black fruits and vegetables. The absorbent biogenic composition is free of non-plant-based pH indicators. The absorbent biogenic composition is free of phenolphthalein and bromothymol blue. The absorbent biogenic composition is free of any non-plant-based compounds or components.

The absorbent biogenic composition may consist of the base material, the plant-based oil, and the plant-based pH indicator. The absorbent biogenic composition may include ingredients that are generally recognized as safe (GRAS). Within 5 minutes after contacting with a liquid having a pH in range between about 6.2 and about 6.8, the absorbent biogenic composition forms a clump having a color in a first color range. Within 5 minutes after contacting with a liquid having a pH less than about 6.2, the absorbent biogenic composition forms a clump having a color in a second color range, where the second color range is outside of the first color range. Within 5 minutes after contacting with a liquid having a pH greater than about 6.8, the absorbent biogenic composition forms a clump having a color in a third color range, where the third color range is outside of the first color range and the second color range. The color in the first color range, the color in the second color range, and the color in the third color range persist for at least 24 hours to one to four weeks. The absorbent biogenic composition has a shelf life of at least about 18 months.

In a second general aspect, preparing an absorbent biogenic composition includes combining a plant-based oil and a plant-based pH indicator to yield a coated pH indicator, and combining the coated pH indicator with a base material to yield the absorbent biogenic composition.

In a third general aspect, preparing an absorbent biogenic composition includes combining a base material and a plant-based pH indicator to yield a mixture, and combining the mixture with a plant-based oil to yield the absorbent biogenic composition.

Implementations of the second and third general aspects may include one or more of the following features. The base material and a plant-based pH indicator are combined using a dry blend mixer.

In a fourth general aspect, a method of preparing an absorbent biogenic composition includes combining a plant-based oil and a base material to yield a coated base material, and combining the coated base material with a plant-based pH indicator to yield the absorbent biogenic composition.

In a fifth general aspect, a method of preparing an absorbent biogenic composition includes combining a base material and a plant-based pH indicator to yield a mixture, and combining the mixture with a plant-based oil to yield the absorbent biogenic composition.

An absorbent biogenic composition including a plant-based chromogenic pH indicator provides litter that is natural and provides a safe experience for animals and owners. In addition, the plant-based pH indicator advantageously allows monitoring of the pH of an animal's urine, which may be indicative of the animal's health. The absorbent biogenic composition is also safe and non-toxic to the animal, and minimizes irritation to internal and external organs of the animal.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

This disclosure describes an absorbent biogenic (e.g., plant-based) composition and a process for making an absorbent biogenic composition. The absorbent biogenic composition is a clumping animal litter. The absorbent biogenic composition includes a plant-based chromogenic pH indicator that changes color based on the pH of liquid (e.g., urine) that contacts the animal litter. The color of the animal litter can be indicative of the health of the animal.

Figure 1:
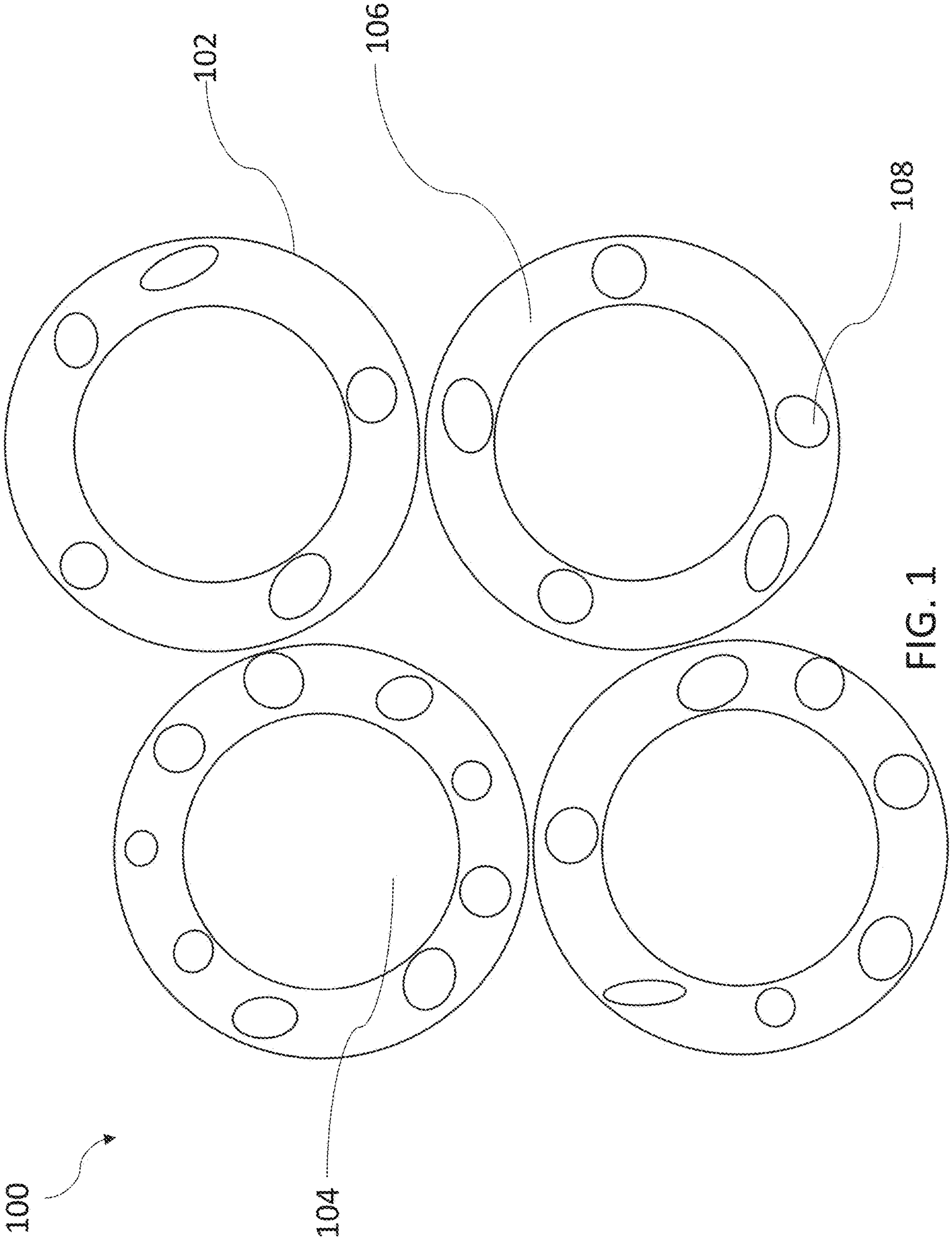
FIG. 1 shows a schematic representation of exemplary particles of an absorbent biogenic composition.

FIG. 1 depicts absorbent biogenic composition 100 with a multiplicity of particles 102. Each particle 102 includes, consists essentially of, or consists of a mixture of a particulate base material 104, a plant-based oil 106, and a plant-based chromogenic pH indicator 108. Absorbent biogenic composition 100 is free of non-biogenic or non-plant-based components. In some cases, the plant-based oil coats the plant-based pH indicator to yield a coated pH indicator. The base material is then combined with the coated pH indicator to yield an absorbent biogenic composition. In some cases, the base material is mixed with the plant-based pH indicator using a dry blend mixer to yield a mixture. The mixture is then combined with the plant-based oil to yield an absorbent biogenic composition. In some cases, the plant-based oil and the base material are combined to yield a coated base material. The coated base material is then combined with the plant-based pH indicator to yield the absorbent biogenic composition.

The base material 104 includes, consists essentially of, or consists of starch, flour, gum, fiber, polysaccharide, protein, cellulose, lignin, or any combination thereof. The polysaccharide may include particulate polysaccharides. Suitable examples of starch include, but are not limited to, corn starch, cassava starch, soybean starch, or any combination thereof. Suitable examples of flour include, but are not limited to, corn flour, cassava flour, soybean flour, or any combination thereof. The absorbent biogenic composition includes at least 98 wt % or at least 99 wt % of the base material.

Suitable examples of plant-based oil 106 include sunflower oil, corn oil, canola oil, cottonseed oil, and soybean oil. In some examples, plant-based oil 106 includes, consists essentially of, or consists of sunflower oil. In one example, the sunflower oil is high oleic sunflower oil (HOSO). The HOSO advantageously provides enhanced oxidative stability relative to other plant-based oils. In some cases, the HOSO provides a longer shelf life than common sunflower oil. The absorbent biogenic composition includes about 0.1 wt % to about 1.0 wt % of the plant-based oil.

The plant-based chromogenic pH indicator can be in the form of a plant-based extractor pigment. The plant-based pH indicator includes, consists essentially of, or consists of a plant-based (e.g., vegetable- or fruit-based) extract in the form of a powder. The plant-based pH indicator can function as an antioxidant. The plant-based pH indicator can include one or more flavonoids (e.g., flavones, isoflavonoids, neoflavonoids, anthocyanins, or any combination thereof) from red, orange, yellow, brown, blue, purple, and black fruits, and vegetables.

Examples of suitable fruits and vegetables include carrots (e.g., black carrots, purple carrots), cabbage (e.g., red cabbages), berries (e.g., blackcurrants, blackberries, blueberries, cranberries, raspberries, strawberries), red onions, kidney beans, pomegranates, grapes, tomatoes, acai, or any combination thereof. The absorbent biogenic composition includes a plant-based chromogenic pH indicator (e.g., a powdered vegetable extract) standardized for a desired amount of chromogenic compound (e.g., flavonoid). The absorbent biogenic composition includes between about 0.001 wt % and about 1 wt % (e.g., between about 0.001 wt % and about 0.01 wt %, between about 0.005 wt % and about 0.5 wt %, between about 0.01 wt % and about 0.1 wt %, between about 0.01 wt % and about 0.05 wt %, between about 0.01 wt % and about 0.04 wt %) of the plant-based chromogenic pH indicator. The absorbent biogenic composition is free of phenolphthalein, bromothymol blue, and other non-plant-based pH indicators.

When the absorbent biogenic composition is contacted with liquid (e.g., urine), a color change occurs. When urine contacts the absorbent biogenic composition, the pH of the urine and chemical components found in the urine effects a visible change in color of the pH indicator. Before contact with liquid, the absorbent biogenic composition is typically white, off-white, light yellow, or cream colored. After contact with urine (e.g., cat urine), the absorbent biogenic composition may transition to a different color (e.g., light pink, pink, strong pink, purple, light blue, blue, strong blue as measured on a spectrophotometric scale) based on the pH of the urine. A pink color is visible at a pH below about 6.2; a purple color is visible at a pH between about 6.2 and about 6.8; and a blue color is visible at a pH above about 6.8.

Figure 2:
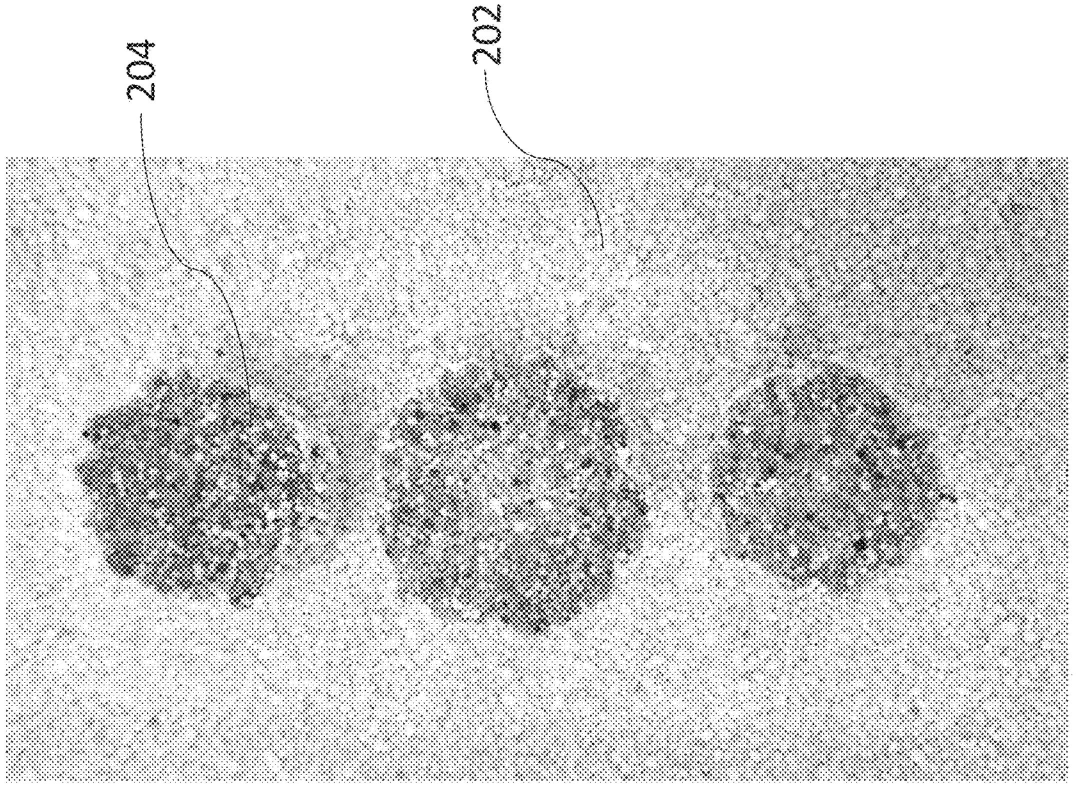
FIG. 2 shows examples of an absorbent biogenic composition in contact with cat urine.

When the absorbent biogenic composition is contacted with urine, an agglomeration of particles (e.g., a clump) is formed. The agglomeration includes particles of the composition adhered together as a result of contact with the urine. FIG. 2 shows some examples of the absorbent biogenic composition before contact with urine 202 and after contact with urine 204. When the absorbent biogenic composition is contacted with urine, a color change occurs. When the urine has a pH in a range between about 6.2 and about 6.8, the absorbent biogenic composition forms a clump having a color in a first color range. The first color range includes colors typically observed with a pH between about 6.2 and about 6.8 given the plant-based pH indicator chosen, which may include shades of purple. When the urine has a pH below about 6.2, the absorbent biogenic composition forms a clump having a color in a second color range. The second color range is different from the first color range. The second color range includes colors typically observed with a pH below about 6.2 given the plant-based pH indicator chosen, which may include shades of pink. When the urine has a pH above about 6.8, the absorbent biogenic composition forms a clump having a color in a third color range. The third color range is different from the first color range and the second color range. The third color range includes colors typically observed with a pH above about 6.8 given the plant-based pH indicator, which may include shades of blue.

Figure 3:
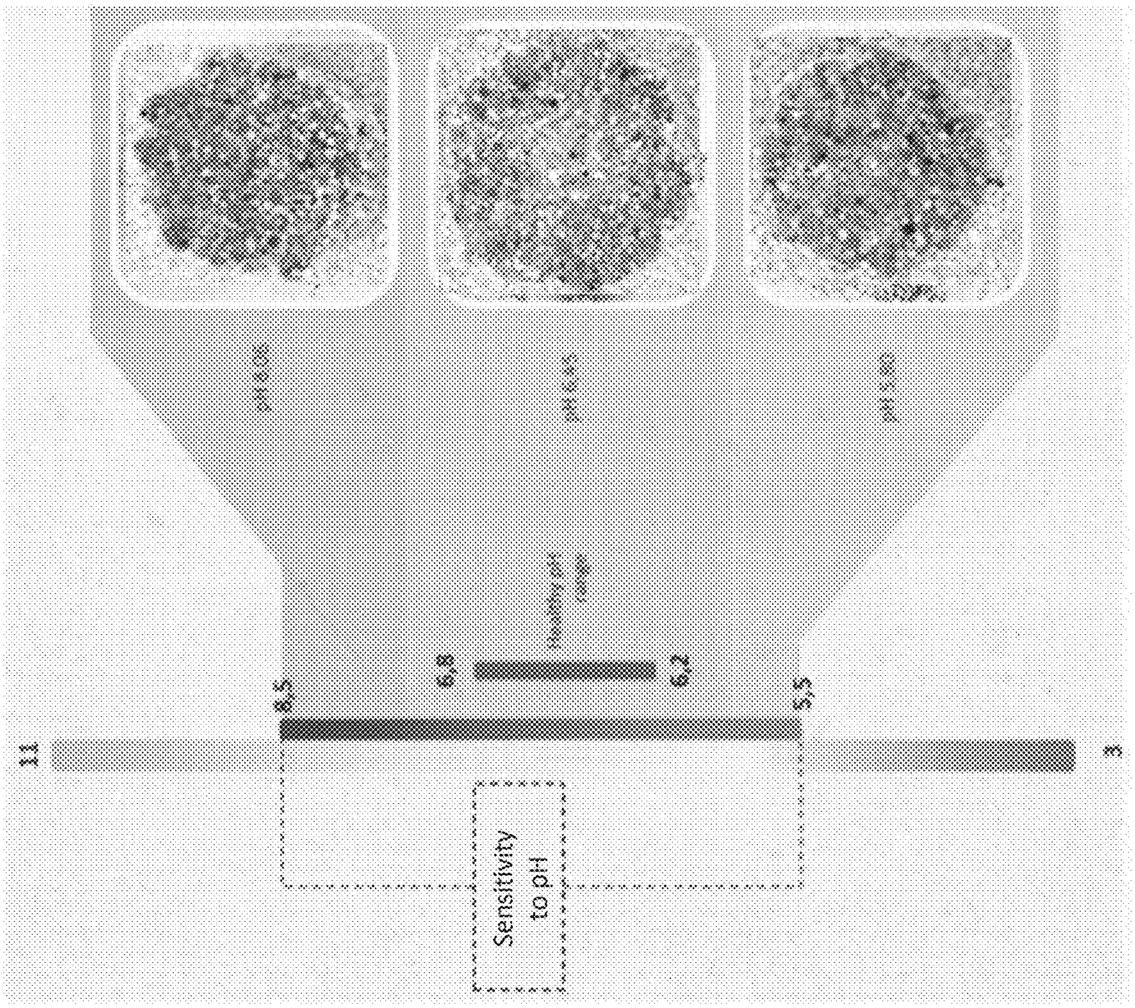
FIG. 3 shows example colors of an absorbent biogenic composition based on varying pH levels of added liquid.

FIG. 3 shows example colors of an absorbent biogenic composition based on varying pH levels of added cat urine. When the urine has a pH of between about 6.2 and about 6.8, the absorbent biogenic composition turns a purple color. When the urine has a pH above about 6.8, the absorbent biogenic composition turns a blue color. When the urine has a pH below about 6.2, the absorbent biogenic composition turns a pink color.

When the absorbent biogenic composition is contacted with urine, the color change stabilizes (e.g., an equilibrium color is reached) within a length of time. The color change of the absorbent biogenic composition stabilizes within 5 minutes after contact with urine. The color of the absorbent biogenic composition after having contacted urine is stable for at least about 24 hours to about one to four weeks.

The stabilized color may indicate the chemical state of the urine (e.g., pH, composition, concentration, or any combination thereof). The stabilized color of the clump can indicate whether the urine is within a normal pH range (e.g., about 6.2 to about 6.8) or outside the range (less than about 6.2 or greater than about 6.8). The stabilized color may indicate the presence or absence of certain compounds in the urine. The stabilized color may indicate whether there is homogeneity in the composition of the urine throughout urination. The stabilized color of the absorbent biogenic composition when observed over multiple instances over time can indicate the overall health of the animal, and thus allow tracking of the animal's health. For a healthy animal, the absorbent biogenic composition may typically turn a characteristic color indicating a characteristic health status. A change in color may indicate a potential health concern. The stabilized color of the clump of the absorbent biogenic composition can allow monitoring of urine pH over time to determine if there is a change due at least in part to one or more physiological, biological, behavioral, or nutritional changes, or any combination thereof.

The absorbent biogenic composition includes ingredients that are generally recognized as safe (GRAS). Generally recognized as safe (GRAS) ingredients include ingredients added to food or other material considered safe by qualified experts under the conditions of intended use. The absorbent biogenic composition is free of any non-biogenic, non-plant-based, or synthetic compounds or components. The absorbent biogenic composition has a shelf life of at least about 18 months under recommended conditions, over which time the composition maintains its ability to absorb liquid and accurately indicate pH, as measured by a spectrophotometer.

Preparing the absorbent biogenic composition includes combining the base material, plant-based oil, and plant-based pH indicator. In a first example, the plant-based oil and the plant-based pH indicator are combined to yield a mixture, and the base material is combined with the mixture. The order of addition in the first example allows the plant-based oil to form a coating over the plant-based pH indicator, and further allows the oil-coated plant-based pH indicator to form a mixture with the base material. In a second example, a base material and a pH indicator (e.g., a powdered plant-based extract, such as a powdered vegetable extract) are blended in a dry blend mixer to yield a mixture, and the plant-based oil is combined with the mixture. The order of addition in the second example allows the plant-based pH indicator to cover the base material, and further allows the plant-based oil to form a coating over the base material and the plant-based pH indicator. In a third example, the plant-based oil and the base material are combined to yield a mixture, and a plant-based pH indicator is combined with the mixture. The order of addition in the third example allows the plant-based oil to form a coating over the base material, and further allows the plant-based pH indicator to combine with the oil-coated base material.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. An absorbent biogenic composition comprising a mixture of:

a base material comprising starch, flour, gum, fiber, polysaccharide, protein, cellulose, lignin, or any combination thereof;

a plant-based oil comprising sunflower oil, corn oil, canola oil, cottonseed oil, soybean oil, or any combination thereof; and a plant-based pH indicator, wherein the plant-based pH indicator is a powdered vegetable extract comprising one or more flavonoids and configured to change color based on a pH of a liquid that contacts the absorbent biogenic composition, and wherein the plant-based pH indicator is coated with the plant-based oil, wherein the absorbent biogenic composition comprises:

at least about 98 wt % of the base material;

about 0.1 wt % to about 1.0 wt % of the plant-based oil, and about 0.001 wt % to about 1.0 wt % of the plant-based pH indicator.

2. The absorbent biogenic composition of claim 1, wherein the absorbent biogenic composition is configured to form a clump when contacted with the liquid.

3. The absorbent biogenic composition of claim 1, wherein the base material comprises starch, and the starch comprises corn starch, potato starch, rice starch, pea starch, soybean starch, or cassava starch.

4. The absorbent biogenic composition of claim 3, wherein the starch comprises cassava starch.

5. The absorbent biogenic composition of claim 1, wherein the base material comprises flour, and the flour comprises corn flour, cassava flour, or soybean flour.

6. The absorbent biogenic composition of claim 5, wherein the flour comprises cassava flour.

7. The absorbent biogenic composition of claim 1, wherein the plant-based oil comprises sunflower oil.

8. The absorbent biogenic composition of claim 7, wherein the sunflower oil comprises high-oleic sunflower oil.

9. The absorbent biogenic composition of claim 1, wherein the one or more flavonoids comprises flavones, isoflavonoids, neoflavonoids, anthocyanins, or a combination thereof.

10. The absorbent biogenic composition of claim 1, wherein the one or more flavonoids are derived from red, brown, orange, yellow, blue, purple, and black fruits and vegetables.

11. The absorbent biogenic composition of claim 10, wherein red, brown, orange, yellow, blue, purple, and black fruits and vegetables comprise black carrots, purple carrots, cabbage, red cabbages, berries, red onions, kidney beans, pomegranates, grapes, tomatoes, acai, or any combination thereof.

12. The absorbent biogenic composition of claim 11, wherein the berries comprise blackcurrants, blackberries, blueberries, cranberries, raspberries, strawberries, or any combination thereof.

13. The absorbent biogenic composition of claim 1, wherein the absorbent biogenic composition is free of non-plant-based pH indicators.

14. The absorbent biogenic composition of claim 13, wherein the absorbent biogenic composition is free of phenolphthalein and bromothymol blue.

15. The absorbent biogenic composition of claim 1, wherein the absorbent biogenic composition is free of any non-plant-based compounds or components.

16. The absorbent biogenic composition of claim 1, wherein the absorbent biogenic composition consists of the base material, the plant-based oil, and the plant-based pH indicator.

17. The absorbent biogenic composition of claim 1, wherein the absorbent biogenic composition has an initial color, and within 5 minutes after contacting the absorbent biogenic composition with a liquid having a pH in range between about 6.2 and about 6.8, the absorbent biogenic composition forms a clump having a color in a first color range, wherein the color in the first color range differs from the initial color.

18. The absorbent biogenic composition of claim 17, wherein, within 5 minutes after contacting the absorbent biogenic composition with a liquid having a pH less than about 6.2, the absorbent biogenic composition forms a clump having a color in a second color range, wherein the color in the second color range differs from the initial color, and the second color range is outside of the first color range.

19. The absorbent biogenic composition of claim 18, wherein, within 5 minutes after contacting the absorbent biogenic composition with a liquid having a pH greater than about 6.8, the absorbent biogenic composition forms a clump having a color in a third color range, wherein the color in the third color range differs from the initial color, and the third color range is outside of the first color range and the second color range.

20. The absorbent biogenic composition of claim 19, wherein the color in the first color range, the color in the second color range, and the color in the third color range persist for at least 24 hours to one to four weeks.

21. The absorbent biogenic composition of claim 19, wherein the color in the third color range is a blue color.

22. The absorbent biogenic composition of claim 18, wherein the color in the second color range is a pink color.

23. The absorbent biogenic composition of claim 17, wherein the color in the first color range is a purple color.

24. A method of preparing the absorbent biogenic composition of claim 1, the method comprising:

combining the plant-based oil and the plant-based pH indicator to yield a coated pH indicator; and combining the coated pH indicator with the base material to yield the absorbent biogenic composition.

25. The absorbent biogenic composition of claim 1, wherein the mixture comprises the base material and the plant-based indicator each coated with the plant-based oil.

26. The absorbent biogenic composition of claim 1, prepared by a process comprising:

combining the plant-based oil and the plant-based pH indicator to yield a coated pH indicator; and combining the coated pH indicator with the base material to yield the absorbent biogenic composition.

27. The absorbent biogenic composition of claim 1, wherein the plant-based pH indicator is standardized for a desired amount of the one or more flavonoids.

28. The absorbent biogenic composition of claim 1, wherein the plant-based pH indicator comprises black carrot extract in the form of a powder.

29. The absorbent biogenic composition of claim 1, wherein the absorbent biogenic composition comprises about 0.005 wt % to 0.5 wt % of the plant-based pH indicator.

30. The absorbent biogenic composition of claim 1, wherein the absorbent biogenic composition comprises about 0.01 wt % to 0.05 wt % of the plant-based pH indicator.

* * * * *